United States Patent [19]
Bair

[11] Patent Number: 5,562,692
[45] Date of Patent: Oct. 8, 1996

[54] FLUID JET SURGICAL CUTTING TOOL

[75] Inventor: Scott Bair, Atlanta, Ga.

[73] Assignee: Sentinel Medical, Inc., Norcross, Ga.

[21] Appl. No.: 438,905

[22] Filed: May 10, 1995

Related U.S. Application Data

[63] Continuation of Ser. No. 96,297, Jul. 26, 1993, abandoned.

[51] Int. Cl.$^6$ ..................................................... A61B 17/32
[52] U.S. Cl. .................................. 606/167; 606/1; 604/22
[58] Field of Search ............................ 604/22, 141, 143, 604/146, 147; 606/159, 127, 1

[56] References Cited

U.S. PATENT DOCUMENTS

| | | | |
|---|---|---|---|
| 3,353,537 | 11/1967 | Knox et al. | 604/143 |
| 3,452,745 | 7/1969 | Hutchinson et al. | |
| 3,515,130 | 6/1970 | Tsujino. | |
| 3,542,017 | 11/1970 | Adams. | |
| 3,561,433 | 2/1971 | Kovach. | |
| 3,605,745 | 9/1971 | Hodosh | 604/143 |
| 3,768,472 | 10/1973 | Hodosh et al. | |
| 3,792,701 | 2/1974 | Kloz et al. | |
| 3,811,795 | 5/1974 | Olsen. | |
| 3,906,954 | 9/1975 | Baehr et al. | |
| 3,930,505 | 1/1976 | Wallach | 604/22 |
| 3,994,297 | 11/1976 | Kopf. | |
| 4,018,623 | 4/1977 | Walker. | |
| 4,278,078 | 7/1981 | Smith. | |
| 4,282,867 | 8/1981 | DuToit. | |
| 4,365,752 | 12/1982 | Waisbren et al. | |

(List continued on next page.)

FOREIGN PATENT DOCUMENTS

| | | | |
|---|---|---|---|
| B6275086 | 3/1987 | Australia | 604/22 |
| 0175096 | 7/1985 | European Pat. Off. | |
| 0253478 | 1/1988 | European Pat. Off. | |
| 0356372 | 2/1990 | European Pat. Off. | |
| 0411170 | 2/1991 | European Pat. Off. | |
| 8706455 | 11/1987 | WIPO. | |

OTHER PUBLICATIONS

Vijay, "A Critical Examination of the Use of Water Jets for Medical Applications", 5th American Water Jet Conference, Aug. 29–31, 1989: Toronto, Canada.

Uchino et al., "Surgical Cutting of the Liver by Water Jet", 9th International Symposium on Jet Cutting Technology, Sendai, Japan: 4–6, Oct. 1988.

Primary Examiner—Corrine M. McDermott
Assistant Examiner—Mark Bockelman
Attorney, Agent, or Firm—Harris Zimmerman

[57] ABSTRACT

A pulsed fluid jet surgical instrument includes a cannula extending from a handpiece, the cannula emitting a pulsed fluid jet for cutting and emulsification purposes, and also providing suction for aspiration and evacuation of the fluid and tissue. A pressure intensifier piston arrangement receives fluid at relatively low pressure, and operates reciprocally and reiteratively to pump the fluid through the jet needle in a series of high pressure pulses, each having a nearly rectangular pressure waveform. The pressure intensifier piston is T-shaped, including a broad end which divides a drive bore into a driving chamber and a retracting chamber. A bistable valve is connected to admit pressure gas into the actuating chamber, driving the piston to translate. The narrow end of the piston is disposed in a fluid pumping chamber connected to a supply of fluid. The translating piston drives the fluid from the pumping chamber through a first check valve into a fluid jet needle, which directs the high pressure fluid pulse to a tissue target. The bistable valve switches to admit pressurized gas to the retracting chamber, driving the piston retrograde and allowing the pumping chamber to refill with fluid through a second check valve. There is no high pressure fluid supplied to the handpiece, and only the pressure intensifying pumping action of the piston creates a high pressure fluid pulse. The gas supply to drive the piston is at a relatively low pressure, so that gas pressure cannot comprise a safety risk to the patient. Thus failure of the piston mechanism cannot result in the emission of a stream of high pressure fluid, and the instrument is inherently safer than prior art instruments that are connected to a high pressure fluid source.

17 Claims, 4 Drawing Sheets

U.S. PATENT DOCUMENTS

| | | | |
|---|---|---|---|
| 4,412,823 | 11/1983 | Sakai et al. . | |
| 4,515,532 | 5/1985 | Walling . | |
| 4,534,340 | 8/1985 | Kerr, . | |
| 4,560,373 | 12/1985 | Sugino et al. . | |
| 4,561,856 | 12/1985 | Cochran . | |
| 4,570,632 | 2/1986 | Woods . | |
| 4,583,531 | 4/1986 | Mattchen . | |
| 4,589,412 | 5/1986 | Kensey | 606/159 |
| 4,655,197 | 4/1987 | Atkinson . | |
| 4,690,672 | 9/1987 | Veltrup | 604/43 |
| 4,705,500 | 11/1987 | Reimels et al. . | |
| 4,764,165 | 8/1988 | Reimels et al. . | |
| 4,776,840 | 10/1988 | Freitas et al. . | |
| 4,790,824 | 12/1988 | Morrow et al. | 604/143 |
| 4,817,599 | 4/1989 | Drews . | |
| 4,861,340 | 8/1989 | Smith et al. | 604/141 |
| 4,898,574 | 2/1990 | Uchiyama et al. | 606/127 |
| 4,913,698 | 4/1990 | Ito et al. | 604/141 |
| 4,944,726 | 7/1990 | Hilal et al. | 604/143 |
| 4,950,238 | 8/1990 | Sullivan | 606/159 |
| 5,019,037 | 5/1991 | Wang et al. | 604/143 |
| 5,033,961 | 7/1991 | Kandler et al. . | |
| 5,037,431 | 8/1991 | Summers et al. | 606/167 |
| 5,046,486 | 9/1991 | Grulke et al. . | |
| 5,049,124 | 9/1991 | Bales, Jr. | 606/159 |
| 5,064,413 | 11/1991 | McKinnon et al. | 604/70 |
| 5,135,482 | 8/1992 | Meracher | 606/159 |
| 5,135,484 | 8/1992 | Wright | 604/22 |
| 5,176,645 | 1/1993 | Guerrero | 604/143 |
| 5,218,956 | 6/1993 | Handler et al. . | |

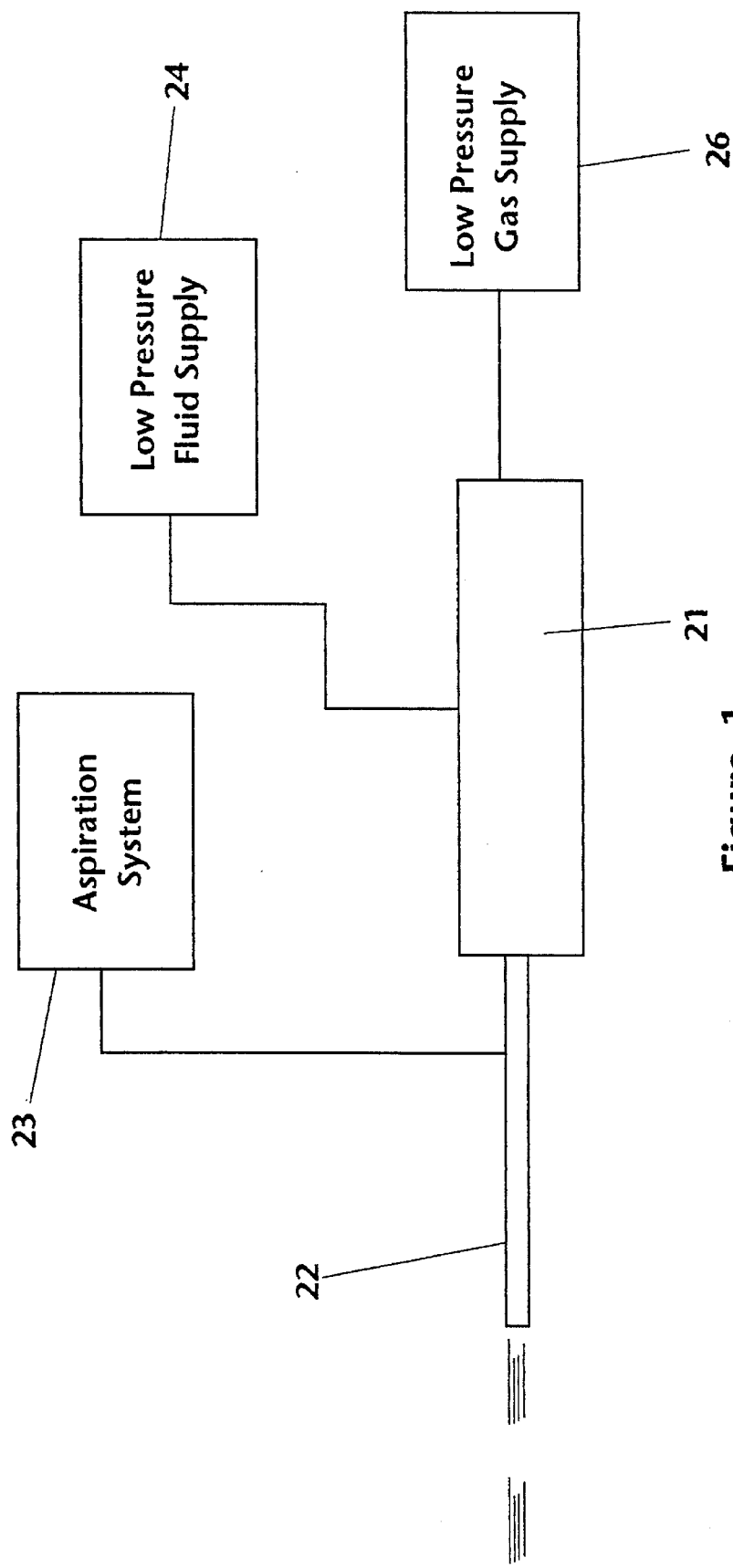

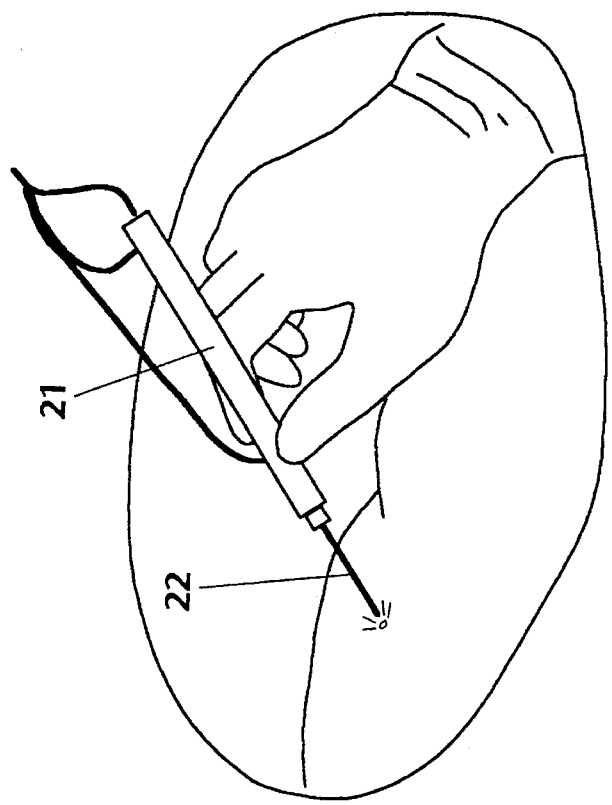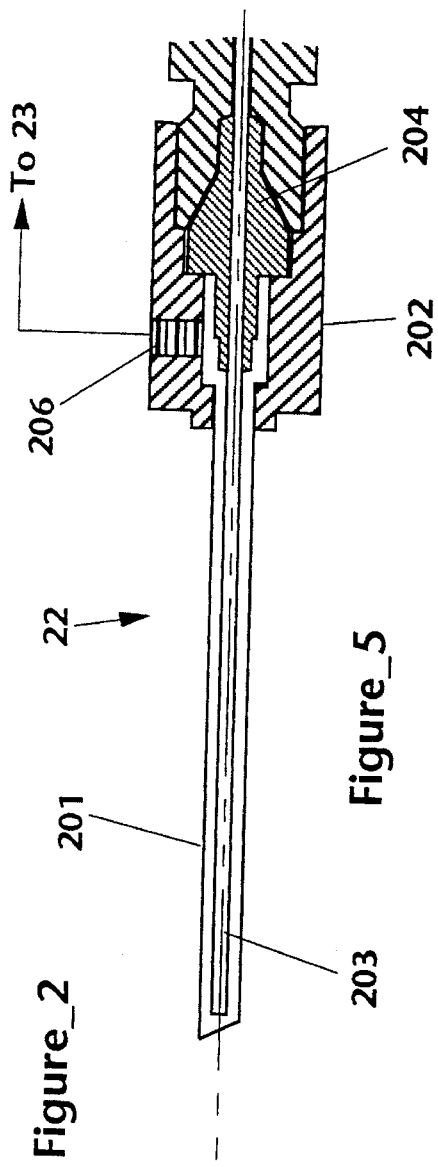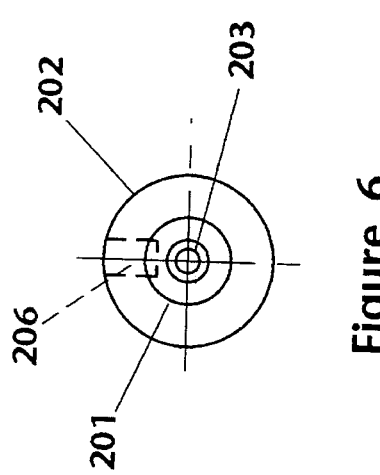

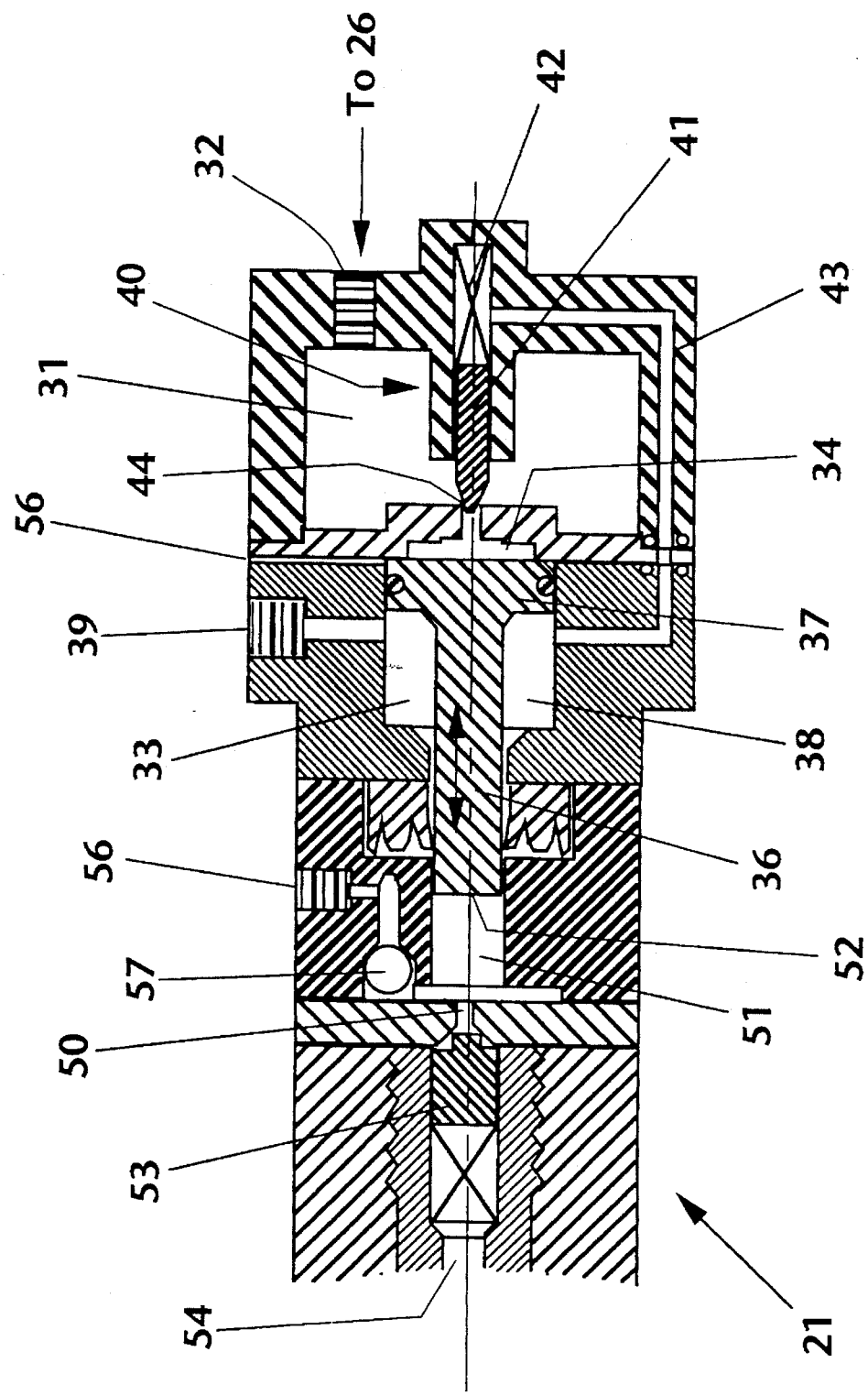
Figure_3

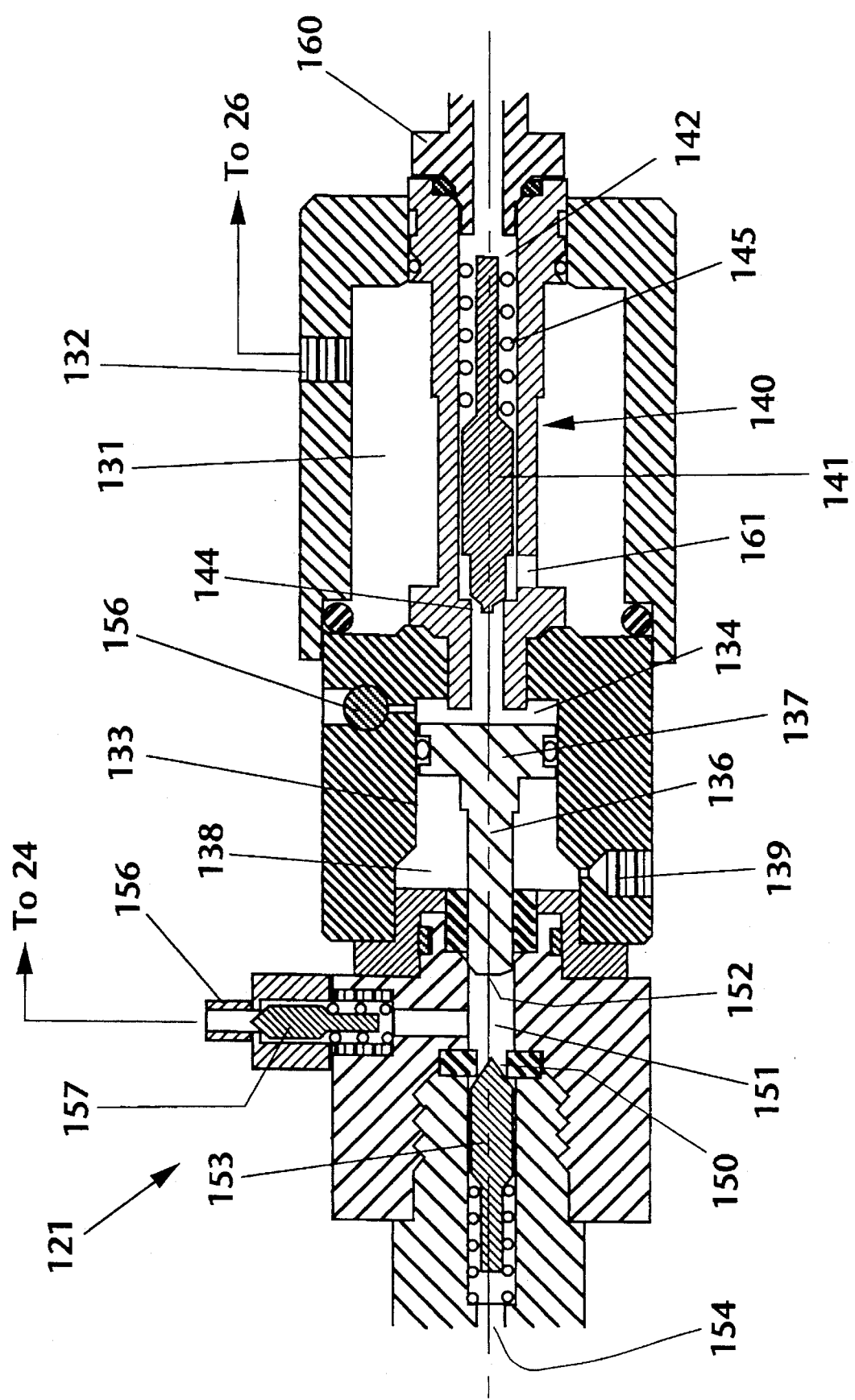
Figure_4

FLUID JET SURGICAL CUTTING TOOL

This is a continuation of application Ser. No. 08/096,297 filed on Jul. 26, 1993 (now abandoned).

BACKGROUND OF THE INVENTION

The present invention generally relates to surgical cutting tools, and more particularly to cutting tools employing a fluid jet as the active cutting agent.

There is currently a great amount of interest in new technologies to replace or supplant traditional surgical cutting tools such as the scalpel. Laser-based tools, electrosurgical cutters, plasma jets, and fluid jets have all been introduced to improve various surgical and medical procedures. Each technology has advantages for particular procedures, as well as intrinsic drawbacks. Fluid jet cutters have several characteristics that make it an attractive new technology. For example, pulsed fluid jet cutters involve no electrical current or voltage, which can comprise a safety risk factor in delicate surgeries. Likewise, there is little heat generated by fluid jets. Indeed, fluid jets are inherently self-cooling. Also, the effects of pulsed fluid jets can be extremely localized and directional, unlike electrosurgical tools and some laser instruments.

Moreover, fluid jet cutters excel at removing soft tissue, due to the fact that high pressure pulsed jets tend to emulsify soft tissue, and the emulsified tissue is easily transported by aspiration away from the surgical site. In contrast, competing technologies such as laser cutters and electrosurgical cutters remove tissue by ablation or electrothermal dissolution. Both of these effects tend to create collateral thermal damage and necrosis, which is generally unwanted and often intolerable for medical purposes.

Indeed, the fact that fluid jet cutting devices include aspiration and evacuation as an integral portion of the device is an added benefit for many surgical procedures. Surgical cutting and excision often involves exsanguination that occludes the surgical field, and the surgeon must employ an assistant to aspirate the field to permit adequate visualization. Fluid jet devices that aspirate the fluid and emulsified tissue also remove the blood and other fluids that might otherwise affect visualization by the surgeon, and they do so without involving additional personnel.

However, fluid jet devices known in the prior art do exhibit some negative characteristics that limit their usefulness. Within restricted body cavities and organs, the volume of fluid introduced by the cutting instrument may exceed the aspiration ability of the instrument, resulting in distention and expansion that can have deleterious side effects. The emulsification effect is primarily a consequence of pulsing the high pressure fluid jet, and the pulse parameters are critical in efficiently emulsifying tissue. Generally speaking, prior art fluid jet tools have not been capable of achieving sufficiently short, well-defined pulses of high pressure fluid to emulsify tissue effectively and completely. Any portion of a fluid pulse that is not delivered at high pressure is ineffective, and merely adds fluid to the surgical field. As a result, a greater volume of fluid is consumed for a given cutting or excision procedure, requiring more time for the surgeon and the provision of more robust aspiration capabilities in the tool.

As a safety measure, it is critical that any fluid jet cutting tool be prevented from emitting a steady stream of high pressure fluid, which can quickly penetrate deeply into soft tissue and can cause catastrophic damage. Some prior art pulsed fluid jet instruments are not designed to inherently prevent a high pressure stream, and must be carefully controlled by external devices to avoid serious accidents.

SUMMARY OF THE INVENTION

The present invention generally comprises a pulsed fluid jet instrument for surgical cutting and excision. A salient feature of the instrument is that it is designed to be inherently safe by preventing the emission of a steady stream of high pressure fluid into tissue. Moreover, the instrument has superior pulse characteristics which optimize cutting and emulsification while minimizing the amount of fluid used in the process.

The instrument of the invention includes a cannula extending from a handpiece, the cannula having an inner needle designed to emit a pulsed fluid jet for cutting and emulsification purposes, and an outer concentric needle or tube connected to a negative pressure source for aspiration and evacuation of the fluid and tissue. The handpiece features a pressure intensifier piston arrangement that receives fluid at relatively low pressure, and operates reciprocally and reiteratively to pump the fluid through the jet needle in a series of high pressure pulses, each having a nearly rectangular pressure waveform.

The pressure intensifier piston is T-shaped, including a broad end which divides a drive bore into an actuating chamber and a retracting chamber. A bistable valve is connected to admit high pressure gas into the actuating chamber, driving the piston to translate. The narrow end of the piston is disposed in a fluid pumping chamber that is connected to a supply of fluid. The translating piston drives the fluid from the pumping chamber through a first check valve into the fluid jet needle, which directs the high pressure fluid pulse to a tissue target. The bistable valve switches to admit pressurized gas to the retracting chamber, driving the piston retrograde and allowing the pumping chamber to refill with fluid through a second check valve.

There is no high pressure fluid supplied to the handpiece, and only the pressure intensifying pumping action of the piston creates a high pressure fluid pulse. Moreover, the gas supply to drive the piston is at a relatively low pressure, so that gas pressure cannot comprise a safety risk to the patient. Thus failure of the piston mechanism cannot result in the emission of a stream of high pressure fluid, and the instrument is inherently safer than prior art instruments that are connected to a high pressure fluid source.

BRIEF DESCRIPTION OF THE DRAWING

FIG. 1 is a functional block diagram of the fluid jet surgical instrument of the present invention.

FIG. 2 is a perspective view showing the fluid jet surgical instrument in use.

FIG. 3 is a cross-sectional view of the pressure intensifier portion of the fluid jet surgical instrument of the present invention.

FIG. 4 is a cross-sectional view of another embodiment of the pressure intensifier portion of the fluid jet surgical instrument.

FIG. 5 is a cross-sectional view of the cannula portion of the fluid jet surgical instrument.

FIG. 6 is an end view of the cannula portion of the fluid jet surgical instrument.

DESCRIPTION OF THE PREFERRED EMBODIMENT

The present invention generally comprises a pulsed fluid jet surgical instrument for cutting, excision, and emulsification and removal of tissue. With reference to FIG. 1, the instrument includes a handpiece 21 adapted to be wielded manually, with a cannula 22 extending therefrom. The cannula emits a pulsed jet of high pressure fluid for surgical cutting and tissue emulsification. The cannula 22 is connected to an aspiration system 23 which provides vacuum aspiration to remove the fluid introduced by the instrument, as well as body fluids and emulsified tissue. The handpiece 21 is also connected to a low pressure fluid supply 24 that provides the fluid which forms the high pressure pulsed cutting jet. A low pressure gas supply 26 is also connected to the handpiece 21 to power the handpiece to produce high pressure fluid pulses.

The instrument is wielded by a surgeon as shown in FIG. 2 to produce surgical cutting and excision effects for therapeutic purposes. It should be noted initially that the handpiece 21 is devoid of any connection to a high pressure source of any kind, so that no failure mode of the invention can introduce a high pressure fluid stream into the patient. Thus the invention is inherently safer than many similar instruments known in the prior art.

With regard to FIG. 3, the handpiece 21 includes an interior gas reservoir 31 that is connected through port 32 to the low pressure gas supply 26. The handpiece also provides a piston 36 having a broad head 37 that is disposed concentrically in a bore 33 in a pressure sealing, translating fashion. The head 37 divides the bore 33 into a driving chamber 34 and a retracting chamber 38. The retracting chamber communicates through port 39 to an actuating valve (not shown) that selectively vents the retracting chamber 38 and permits pulsed operation of the unit. The actuating valve may comprise a pneumatic switch on the handpiece, or a footswitch coupled by tubing to the port 39.

The handpiece further includes a bistable valve assembly 40, comprised of a valve pintle 41 slidably disposed in a bore 42. The bore 42 is connected through passageway 43 to the retracting chamber 38 of the bore 33. A valve port 44 extends from the driving chamber 34 to the gas reservoir 31, and the tip of the valve pintle 41 seats in the port 44 to selectively block gas flow from the reservoir to the driving chamber. A compression spring is disposed in the bore 42 to bias the pintle to close the port 44.

The piston 36 includes a narrow pumping end 52 disposed in a pump chamber 51. The pump chamber 51 communicates through an outlet passage 50 to a relief valve 53, which in turn leads to a tube 54 connected to the jet outlet port. The relief valve is set to open at a relatively high pressure, so that no fluid flow is admitted to the jet outlet port until pressure in the pump chamber attains a high value. With this arrangement, the jet pulses are comprised solely of high pressure fluid, and the pressure versus time profile of each pulse approaches a rectangular waveform. Fluid such as sterile saline solution, Ringer's solution, or the like is supplied to the pump chamber from supply 24 through inlet port 56 and ball check valve 57.

To operate the apparatus depicted in FIG. 3, the actuating valve connected to port 39 is opened, venting the retracting chamber to ambient pressure. The pressure in bore 42 likewise drops, due to the flow communication of passageway 43, and the gas pressure in reservoir 31 overcomes the spring force acting on the pintle 41. The pintle 41 is driven into the bore 42, opening the port 44 and admitting pressurized gas from the reservoir 31 into the driving chamber 34. The piston translates toward the jet tube 54, compressing the fluid in the pump chamber 51. When the pressure in the fluid chamber exceeds the threshold of the relief valve 53, fluid is expelled through the jet tube 54 as a high pressure fluid pulse.

It is significant to note that driving surface of the piston head 37 is far greater in area than the pump end 52, and that the force developed at the head 37 is transmitted to a far smaller fluid surface area in the pump chamber. As a result, the gas pressure driving the piston is greatly amplified (on the order of ten times or more), thereby creating a very high pressure pulse from a low pressure fluid supply and a low pressure gas supply. For example, fluid may be provided at approximately 100 psig, and the relief valve may be set to open at 300 psid or more. The maximum pressure developed during the pressure pulse may exceed 1000 psig, even though the gas pressure supplied to the instrument may be 100–120 psig.

When the actuating valve is closed, gas pressure leaking past the pintle 41 and through the passageway 43 begins to build pressure in the retracting chamber 38. Pressure also builds in the bore 42, urging the pintle to translate and seal the inlet port 44. Gas pressure bleeds from the driving chamber 34 through a bleed passage 56, and the piston retracts. The relief valve 53 closes when the piston begins to retract, and inlet valve 57 opens to permit the pump chamber to refill. Thus one high pressure fluid jet pulse is completed, and the apparatus is set to deliver another pulse. However, it should be noted that the actuating valve must be reopened to initiate another pulse, and that the mechanism is not free-running. Thus there is no possibility of the instrument delivering additional pulses after shutdown is desired, and the apparatus is inherently safe in another important characteristic.

With regard to FIG. 4, a further embodiment 121 of the handpiece is designed to optimize the mechanical design of the instrument for efficient manufacturing, cleaning, and servicing. The handpiece 121 includes an interior gas reservoir 131 that is connected through side port 132 to the low pressure gas supply 26. The handpiece includes a piston 136 having a broad head 137 that is disposed concentrically in a bore 133 in a pressure sealing, translating fashion. The head 137 divides the bore 133 into a driving chamber 134 and a retracting chamber 138. The retracting chamber communicates through port 139 to an actuating valve (not shown) that selectively vents the retracting chamber 138 to permit pulsed operation of the unit. The actuating valve may comprise a pneumatic switch on the handpiece, or a footswitch coupled by tubing to the port 139. A bleed port 156 extends from the driving chamber 134 to ambient atmosphere.

The handpiece further includes a bistable valve assembly 140, comprised of a valve pintle 141 slidably disposed in a bore 142. A valve port 144 extends from the driving chamber 134 through port 161 to the gas reservoir 131, and the tip of the valve pintle 141 seats in the port 144 to selectively block gas flow from the reservoir to the driving chamber. A compression spring 145 is disposed in the bore 142 to bias the pintle to close the port 144. A connector 160 is coupled to the outer end of the bore 142, and is connected to join the bore 142 in flow communication with the port 139 of the retracting chamber 138.

The piston 136 includes a narrow pumping end 152 disposed in a pump chamber 151. The pump chamber 151 communicates through an outlet passage 150 to a relief valve 153, which in turn leads to a tube 154 connected to the jet outlet port. The relief valve is set to open at a relatively high pressure, so that no fluid flow is admitted to the jet outlet port until pressure in the pump chamber attains a high value. With this arrangement, the jet pulses are comprised solely of high pressure fluid, and the pressure versus time profile of each pulse approaches a rectangular waveform. Fluid such as sterile saline solution, Ringer's solution, or the like is supplied to the pump chamber from supply 24 through inlet port 156 and check valve 157.

To operate the apparatus 121, the actuating valve connected to port 139 and 160 is opened, venting the retracting chamber to ambient pressure. The pressure in bore 142 likewise drops, due to the flow connection between port 139 and connector 160, and the gas pressure delivered through port 161 from reservoir 131 overcomes the spring force acting on the pintle 141, The pintle 141 is driven into the bore 142, opening the port 144 and admitting pressurized gas from the reservoir 131 into the driving chamber 134. The piston translates toward the jet tube 154, compressing the fluid in the pump chamber 151. When the pressure in the fluid chamber exceeds the threshold of the relief valve 153, fluid is expelled through the jet tube 154 as a high pressure fluid pulse.

When the actuating valve is closed, gas pressure leaking past the pintle 141 and through the connection to port 139 begins to build pressure in the retracting chamber 138. Pressure also builds in the bore 142, allowing the spring 145 to urge the pintle to translate and seal the inlet port 144. Gas pressure bleeds from the driving chamber 134 through the bleed passage 156, and the higher pressure in the retracting chamber causes the piston 136 to retract. The relief valve 153 closes when the piston begins to retract, and inlet valve 157 opens to permit the pump chamber to refill. Thus one high pressure fluid jet pulse is completed, and the apparatus is set to deliver another pulse. As in the previous embodiment, the actuating valve must be reopened to initiate another pulse, and the mechanism is not free-running. Thus there is no possibility of the apparatus delivering additional pulses after shutoff is desired.

With regard to FIGS. 5 and 6, the cannula assembly 22 of the invention includes an aspiration tube 201 extending coaxially and distally from a housing 202. A jet tube 203 is disposed concentrically and coaxially within the aspiration tube 201, and is supported by a mandrel 204 secured within the housing 202. The distal end of the jet tube is recessed slightly within the distal end of the aspiration tube, and the proximal end of the jet tube is connected to the high pressure pulse output 54 or 154 described previously. The interior of the housing 202 communicates with the interior space of the aspiration tube 201, and port 206 connects the aspiration tube to the aspiration system 23 described previously. The housing 202 is joined to either of the handpieces 21 or 121 described above.

The distal end of the jet tube 203 emits a train of pulses of high pressure fluid from the handpiece apparatus, causing the target tissue to be cut and emulsified. The suction provided by the aspiration tube removes the fluid emitted by the jet tube, as well as the emulsified tissue and body fluids, so that surgical cutting and tissue excision and removal may be carried out quickly and efficiently.

I claim:

1. A fluid jet surgical cutting instrument, comprising:

cannula means for directing a plurality of high pressure fluid pulses toward a tissue target and for aspirating fluid and emulsified tissue from the vicinity of the tissue target;

handpiece means for supporting said cannula means such that said cannula means extends from a distal end of said handpiece means, said handpiece means including connecting means for receiving low pressure fluid and pressurized gas from external sources; and pressure intensifier means disposed within said handpiece means for generating said high pressure fluid pulses within said handpiece means from said low pressure fluid and said pressurized gas and delivering said high pressure fluid pulses to said cannula means for delivery to said tissue target.

2. The fluid jet surgical cutting instrument of claim 1, wherein said pressure intensifier means includes a piston disposed within said handpiece means, said piston having a first end adapted to be driven reciprocally by said pressurized gas, and a second end adapted to pump said low pressure fluid and form said high pressure fluid pulses for delivery to said cannula means.

3. The fluid jet surgical cutting instrument of claim 2, wherein said first end of said piston is disposed within a first bore, said first bore including a driving chamber and a retracting chamber.

4. The fluid jet surgical cutting instrument of claim 3, further including first valve means for providing said pressurized gas to said driving chamber and said retracting chamber in serial, alternating fashion to drive said piston to reciprocate.

5. The fluid jet surgical cutting instrument of claim 4, wherein said handpiece means include a valve bore and said first valve means includes a valve pintle, said valve pintle disposed in said valve bore, said valve pintle being reciprocable within said valve bore to admit said pressurized gas to said driving chamber.

6. The fluid jet surgical cutting instrument of claim 5, wherein said valve bore communicates at a first end with said retracting chamber, said pintle being reciprocable in said valve bore to alternatingly open and close said first end to communicate said bore with said retracting chamber.

7. The fluid jet surgical cutting instrument of claim 6, wherein said valve bore communicates at a second end with said pressurized gas.

8. The fluid jet surgical cutting instrument of claim 7, wherein said handpiece means includes an inlet port, said inlet port in communication with said driving chamber to admit said pressurized gas therein, said valve pintle disposed to selectively block and open said inlet port.

9. The fluid jet surgical cutting instrument of claim 8, further including vent means for venting said retracting chamber and said first end of said valve bore to ambient pressure, whereby said pressurized gas drives said valve pintle to open said inlet port and admit pressurized gas to said driving chamber and urge said piston to translate in a pumping stroke.

10. The fluid jet surgical cutting instrument of claim 9, further including pressure bleed means for venting said driving chamber such that gas pressure in said retracting chamber urges said piston to retract from said pumping stroke.

11. The fluid jet surgical cutting instrument of claim 9, further including compression spring means for resiliently biasing said valve pintle toward said second end of said valve bore to close said inlet port.

12. The fluid jet surgical cutting instrument of claim 8, wherein said handpiece means further includes a pressurized gas reservoir chamber, said inlet port connecting said driving chamber and said gas reservoir chamber.

13. The fluid jet surgical cutting instrument of claim 6, further including a conduit means extending from said retracting chamber to said first end of said valve bore externally of said handpiece means.

14. The fluid jet surgical cutting instrument of claim 6, wherein said handpiece means includes an internal passage extending between said retracting chamber and said first end of said valve bore.

15. The fluid jet surgical cutting instrument of claim 3, wherein said second end of said piston is disposed in a pump bore, said pump bore being in communication with said cannula means.

16. The fluid jet surgical cutting instrument of claim 15, further including a high pressure relief valve interposed between said pump bore and said cannula means to admit only high pressure fluid to said cannula means.

17. The fluid jet surgical cutting instrument of claim 16, further including check valve means for admitting said low pressure fluid to said pump bore.

* * * * *